United States Patent
He et al.

(10) Patent No.: US 10,966,755 B2
(45) Date of Patent: Apr. 6, 2021

(54) IMPLANT DELIVERY APPARATUS

(71) Applicant: SHANGHAI MICROPORT CARDIOFLOW MEDTECH CO., LTD., Shanghai (CN)

(72) Inventors: Zhixiu He, Shanghai (CN); Baozhu Gui, Shanghai (CN); Yu Li, Shanghai (CN)

(73) Assignee: SHANGHAI MICROPORT CARDIOFLOW MEDTECH CO., LTD., Shanghai (CN)

( * ) Notice: Subject to any disclaimer, the term of this patent is extended or adjusted under 35 U.S.C. 154(b) by 231 days.

(21) Appl. No.: 16/343,562

(22) PCT Filed: Sep. 22, 2017

(86) PCT No.: PCT/CN2017/102959
§ 371 (c)(1),
(2) Date: Apr. 19, 2019

(87) PCT Pub. No.: WO2018/072595
PCT Pub. Date: Apr. 26, 2018

(65) Prior Publication Data
US 2020/0046406 A1    Feb. 13, 2020

(30) Foreign Application Priority Data

Oct. 20, 2016   (CN) .......................... 201610916660.3

(51) Int. Cl.
*A61B 17/34*    (2006.01)
*A61B 17/00*    (2006.01)
(Continued)

(52) U.S. Cl.
CPC .... *A61B 17/3468* (2013.01); *A61B 17/00234* (2013.01); *A61F 2/2436* (2013.01);
(Continued)

(58) Field of Classification Search
CPC ...... A61F 2/2427–2439; A61F 2/95–97; A61F 2/011; A61B 2017/1205–12095; A61B 17/3468; A61B 2017/00623
See application file for complete search history.

(56) References Cited

U.S. PATENT DOCUMENTS 5,700,269 A * 12/1997 Pinchuk ............... A61B 5/1076
606/108
2005/0090890 A1 * 4/2005 Wu .................... A61M 25/0021
623/1.11
(Continued)

FOREIGN PATENT DOCUMENTS

CN    101553190 A    10/2009
CN    102497907 A    6/2012
(Continued)

*Primary Examiner* — Darwin P Erenzo
*Assistant Examiner* — Brigid K Byrd
(74) *Attorney, Agent, or Firm* — Muncy, Geissler, Olds & Lowe, P.C.

(57) ABSTRACT

An implant delivery device (100) includes a casing (110); and inner and outer tube driving members (150, 160), an inner tube (120), an intermediate tube (130), an outer tube (140) and an air-evacuation locking assembly (170), each at least partially accommodated in the casing (110). The three tubes are sequentially nested in one another, and first, second and third spaces are formed between neighbouring tubes. The inner tube driving member (150) has a proximal end that is sealingly fixed to a proximal end of the inner tube (120), and the outer tube driving member (160) is sealingly fixed to a proximal end of the outer tube (140). The intermediate tube (130) has a proximal end that is sealingly fixed to the inner tube driving member (150), and the intermediate tube extends through and is sealingly connected to the outer tube driving member (160). The air-evacuation locking assembly (170) is detachably coupled to the inner tube driving member (150). The inner tube driving member (150) and the
(Continued)

air-evacuation locking assembly (170) are provided with first and second air-evacuation channels (A, B), respectively. When the air-evacuation locking assembly (170) is coupled to the inner tube driving member (150), the second air-evacuation channel (B) is brought into communication with the second and third spaces via the first air-evacuation channel (A) and the first space. The inner tube driving member (150) is coupled to the casing (110) by the air-evacuation locking assembly (170). When the air-evacuation locking assembly (170) is disconnected from the inner tube driving member (150), the inner tube driving member (150) remains in slidable connection with the casing (110).

15 Claims, 7 Drawing Sheets

(51) Int. Cl.
*A61F 2/24* (2006.01)
*A61F 2/95* (2013.01)

(52) U.S. Cl.
CPC ............... *A61B 2017/00243* (2013.01); *A61B 2017/00969* (2013.01); *A61F 2/9517* (2020.05)

(56) References Cited

U.S. PATENT DOCUMENTS

| | | | |
|---|---|---|---|
| 2009/0287182 | A1 | 11/2009 | Bishop et al. |
| 2011/0264199 | A1* | 10/2011 | Tran ...................... A61F 2/2436 |
| | | | 623/2.11 |
| 2013/0116771 | A1 | 5/2013 | Robinson |

FOREIGN PATENT DOCUMENTS

| | | |
|---|---|---|
| CN | 102764165 A | 11/2012 |
| CN | 204709078 U | 10/2015 |
| CN | 206499552 U | 9/2017 |

* cited by examiner

IMPLANT DELIVERY APPARATUS

TECHNICAL FIELD

The present invention relates to the technical field of medical devices and, in particular, to an implant delivery device.

BACKGROUND

Heart valve diseases are some of the most frequently diagnosed cardiac diseases in China, and are found to be mostly heart valve damage caused by rheumatic fever. In recent years, the continually aging population has driven an increasing incidence of valvular degeneration (including calcification, mucoid degeneration, etc.) and valvular damage caused by metabolic disorders. Heart valve replacement surgeries are conventionally open-heart procedures conducted under general anesthesia, during which, following an incision made along the patient's sternum (commonly known as "sternotomy"), and the heart is stopped and blood flow is guided through a "heart-lung" bypass machine (also known as "extracorporeal circulation machine"). Therefore, such traditional open surgeries are associated with a high risk and bring to patients significant traumas as well as possible transient disturbances caused by emboli and other issues arising from the use of heart-lung machine. Complete recovery from the traumas typically costs a couple of months. For some special population groups such as elders, the traumas are particularly unendurable and the recovery needs more time and is sometime even impossible. Thus, the advent of minimally invasive interventional therapy has undoubtedly given more hope to patients with heart valve diseases.

Minimally invasive interventional therapies offer a variety of advantages, including needlessness of sternotomy, minimal traumas and quick patient recovery and have found intensive use in recent years. In particular, their application in the recent decade shows that this minimally invasive interventional therapeutic methodology is able to cope with not only all diseases curable by traditional medical and surgical treatments but also some diseases that the traditional approaches could not handle. In view of the widespread use of minimally invasive interventions in clinics, more in-depth research is sensible in this field.

A minimally invasive interventional procedure for heart valve replacement involves implanting a prosthetic heart valve in the body of a patient by using a delivery device. However, since the operation of existing delivery devices for such prosthetic heart valves tends to be complicated and require high skill of the operating physician, they suffer from frequent operational troubles. For example, after the prosthetic heart valve is delivered to and deployed at the target site, the existing delivery devices often cause secondary damage to the patient's body during retrieval therefrom. In addition, the existing delivery devices are designed with a hose leading from a space between an outer tube and an inner tube and connected to an external device for introducing a fluid into the hose and driving the fluid in the hose to flow through the aforesaid space so as to expel the air there out of the system, which may interfere with the interventional procedure. However, during the packaging and transportation of the delivery devices, the hose is required to be fixed in addition to the delivery devices themselves. During the fixation, it is very likely for the hose to be crushed or flexed. Further, since there is no fixation rail along which the hose can move in a lumen of a handle, when the delivery device is advanced or retracted during the procedure, it is likely for the hose to be flexed as a result of the movement of the outer or inner tube and thus make the air evacuation difficult.

SUMMARY OF THE INVENTION

It is an object of the present invention to provide an implant delivery device to solve one or more of the above-described problems in the prior art.

To this end, the present invention provides an implant delivery device, comprising: a casing; and an inner tube driving member, an outer tube driving member, an inner tube, an intermediate tube, an outer tube and an air-evacuation locking assembly, each at least partially accommodated in the casing. The inner tube, the intermediate tube and the outer tube are sequentially nested from inside to outside. The inner tube and the intermediate tube form a first space therebetween, and the intermediate tube and the outer tube form a second space therebetween. The inner tube and the outer tube form a third space therebetween.

The inner tube driving member has a proximal end that is sealingly fixed to a proximal end of the inner tube, and the outer tube driving member is sealingly fixed to a proximal end of the outer tube. The intermediate tube has a proximal end that is sealingly fixed to the inner tube driving member, and the intermediate tube extends through and is sealingly connected to the outer tube driving member. The air-evacuation locking assembly is detachably coupled to the inner tube driving member.

The inner tube driving member is provided with a first air-evacuation channel, and the air-evacuation locking assembly is provided with a second air-evacuation channel. The second air-evacuation channel protrudes out of the casing at a first end and is brought, at a second end, into communication with the second and third spaces via the first air-evacuation channel and the first space when the air-evacuation locking assembly is coupled to the inner tube driving member. The inner tube driving member is axially fixable relative to the casing through the air-evacuation locking assembly and, when the air-evacuation locking assembly is disconnected from the inner tube driving member, the inner tube driving member is axially slidable along the casing.

Preferably, the air-evacuation locking assembly may comprise a locking member which is detachably coupled to the inner tube driving member and comprises a lumen extending through the locking member to form the second air-evacuation channel.

Preferably, the locking member may comprise a stopper section detachably connectable to the inner tube driving member and a controller section for driving the stopper section to move, the controller section having a first end located outside the casing and provided with a first lumen extending through the controller section, the stopper section provided with a second lumen extending through the stopper section, the first lumen and the second lumen communicating with each other to form the second air-evacuation channel.

Preferably, the implant delivery device may further comprises a guide member provided within the casing, wherein the guide member comprise a guide channel extending therethrough and the stopper section is movable relative to the inner tube driving member along an extending direction of the guide channel.

Preferably, the inner tube driving member may comprise a third lumen and a fourth lumen, the third lumen axially extending through the inner tube driving member, the third lumen having a distal end in coincidence with the proximal end of the intermediate tube and a proximal end in coincidence with the proximal end of the inner tube, the fourth lumen constituting the first air-evacuation channel and communicating with the first space.

Preferably, the outer tube driving member may comprise a fifth lumen extending therethrough axially, in which the proximal end of the outer tube is located, wherein the intermediate tube extends from the inner tube driving member through the fifth lumen.

Preferably, the air-evacuation locking assembly may comprise a locking member detachably coupled to the inner tube driving member and a fluidic member in fixed connection with the locking member, the locking member having a portion situated out of the casing and comprising a sixth lumen in communication with the first air-evacuation channel, the fluidic member comprising a seventh lumen extending therethrough, the sixth and seventh lumens communicating with each other to form the second air-evacuation channel.

Preferably, the locking member may comprise a stopper section detachably connectable to the inner tube driving member and a controller section for driving the stopper section to move, wherein the controller section has a first end located outside the casing, and the stopper section are provided with the sixth lumen.

Preferably, the stopper section may comprise a stopper body detachably coupled to the inner tube driving member and an elastic structure coupled to the stopper body, wherein the stopper section is connected to the inner tube driving member via the elastic structure and, when the elastic structure is stressed, the stopper section is disconnected from the inner tube driving member.

Preferably, the air-evacuation locking assembly may comprise a flow control member for controlling a flow direction of an air-evacuation medium. The flow control member may be disposed in the second air-evacuation channel.

Preferably, the flow control member may comprise a one-way check valve or a controllable lock valve.

Preferably, the intermediate tube may be provided with, at the distal end, an air-evacuation aperture through which the first space communicates with the second space, wherein when the air-evacuation locking assembly is coupled to the inner tube driving member, the second end of the second air-evacuation channel is brought into communication with the second and third spaces via the first air-evacuation channel, the first space and the air-evacuation aperture.

Preferably, the intermediate tube may comprise a plurality of air-evacuation apertures that are uniformly distributed around a circumference of the intermediate tube.

Preferably, the distal end of the intermediate tube may be fixed but not sealed to the inner tube.

Preferably, the implant delivery device may further comprise a movement control member and a move guide track, the move guide track disposed on the casing, the movement control member movably disposed on the move guide track and coupled to the outer tube driving member.

In summary, the inner tube in the implant delivery device of the present invention can be either coupled to or made movable relative to the casing by virtue of the engagement or disengagement between the inner tube driving member and the air-evacuation locking assembly, depending on the actual need. As such, when the delivery device is retrieved after the deployment of implant, the outer tube is kept stationary, the inner tube driving member can be unlocked from the air-evacuation locking assembly such that the inner tube can be moved in the casing and further to drive the inner tube to approach, abut against and thereby close the outer tube, then the delivery device is retrieved from the patient's body. Since a sheath arranged at the distal end of the outer tube is required to constrain the implant in a crimped configuration, it is necessary for the sheath to be relatively rigid. For this reason, conventionally, driving the inner and outer tubes to abut each other to achieve the closure after the deployment of the implant tends to cause secondary damage to the patient's body by the sheath. In contrast, according to the present invention, the inner tube has smaller size and is made of a more bendable and softer material, and the inner tube is allowed by a displacement to abut at the distal end against the distal end of the outer tube and hence close the outer tube. This can lower the risk of secondary damage to the patient's body during retrieval. In addition, in the implant delivery device of the present invention, the second air-evacuation channel arranged in the air-evacuation locking assembly is brought into communication with the second space between the intermediate tube and the outer tube and the third space between the outer tube and the inner tube via the first air-evacuation channel in the inner tube driving member and the first space between the intermediate tube and the inner tube, enabling evacuation of the air from between the inner tube and the outer tube. By using the air-evacuation locking assembly in replace of an air-evacuation hose, this design solves the problem of a deformed or clogged air-evacuation path that may make it hardly possible to expel the air out of the system, arising from the use of the air-evacuation hose. Further, this integral design of the air-evacuation and locking integrates the air-evacuation and locking functions, thus reducing the number of required components and simplifying the operational process. As a result, the delivery device can be more conveniently used with increased performance robustness.

Figure 1:
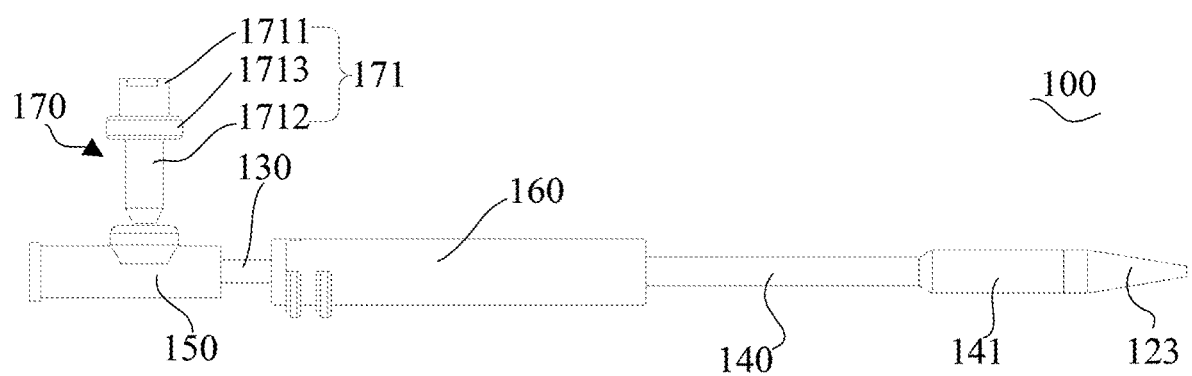
FIG. 1 is a schematic illustration of an implant delivery device according to Embodiment 1 of the present invention, in which a casing is not shown.

LIST OF REFERENCE NUMERALS IN DRAWINGS 100, 200 implant delivery device
110 casing
120 inner tube
121 anchor
122 distal section of the inner tube
123 conical tip
130 intermediate tube
131 air-evacuation aperture
140 outer tube
141 sheath
150, 220 inner tube driving member
160 outer tube driving member
170, 210 air-evacuation locking assembly
171, 211 locking member
1711, 2111 controller section
1712, 2112 stopper section
1713, 2123 flow control member
2113 stopper body
2114 elastic structure
212 fluidic member
2121 body of fluidic member
2122 connecting pipe
1714, 1715 check orifice
180 guide member
190 sealing ring
230 support member
A first air-evacuation channel
B second air-evacuation channel

DETAILED DESCRIPTION

The implant delivery device according to the present invention will be described in further detail below with reference to FIGS. 1 to 11 so that objects, advantages and features of the invention will appear clearer. Note that the figures are much simplified and may not be drawn to scale, and their sole purpose is to facilitate easy and clear explanation of the embodiments.

As used herein and in the appended claims, the term "or" is intended to mean "and/or", unless the context clearly indicates otherwise. The term "distal end" refers to an end far away from a person who is operating the device, while the term "proximal end" means an end close to the operating person.

Throughout the figures, like reference numerals indicate like elements. The implant delivery device of the present invention can be used to deliver an implant (e.g., a prosthetic heart valve) to a target site in the body and deploy the implant at the target site.

Embodiment 1

Figure 2:
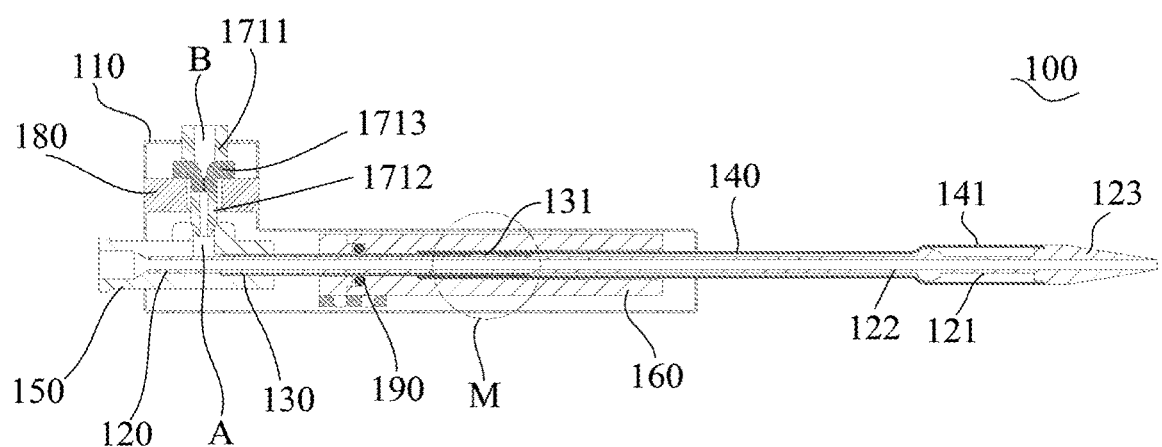
FIG. 2 is a diagram schematically illustrating an air-evacuation locking assembly connected to an inner tube driving member in the implant delivery device according to Embodiment 1 of the present invention.
Figure 3:
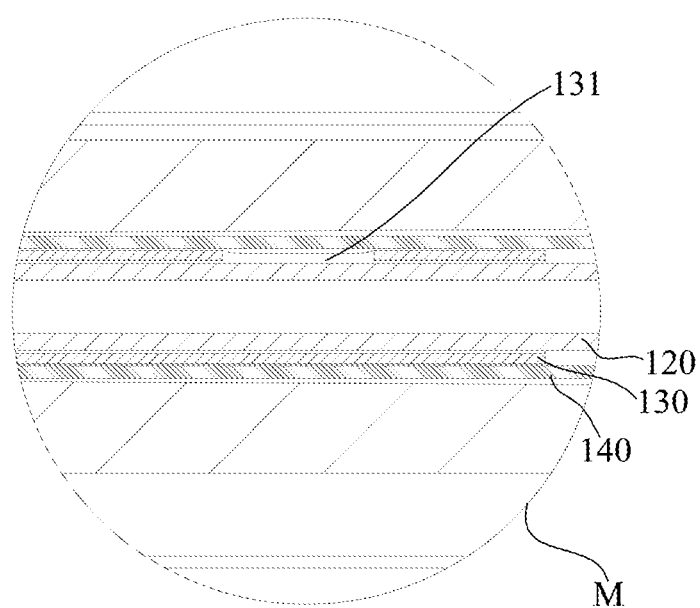
FIG. 3 is an enlarged view of portion M of the implant delivery device of FIG. 2.
Figure 4:
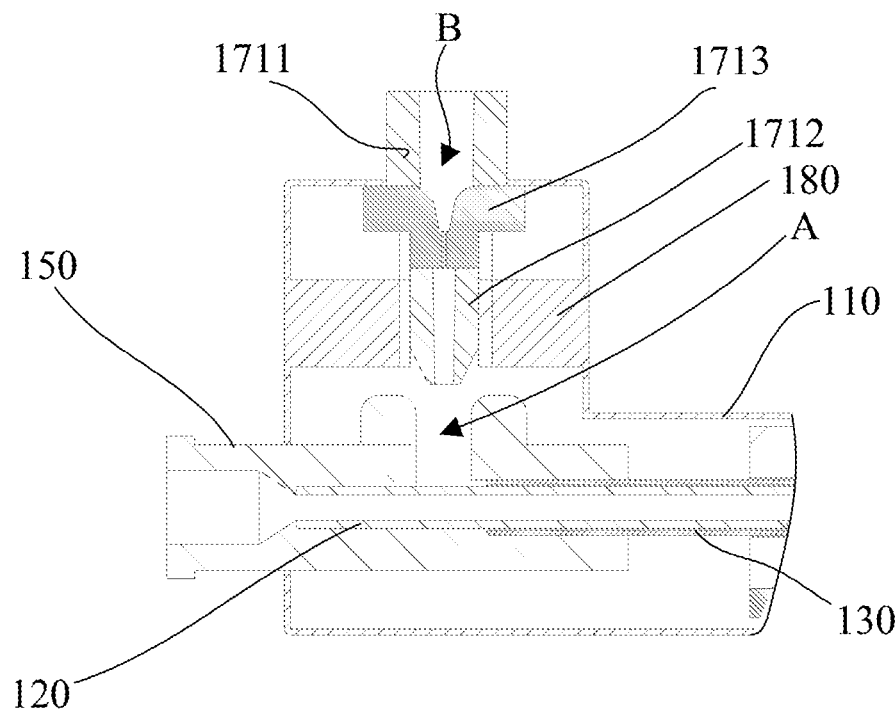
FIG. 4 is a partial schematic illustrating the air-evacuation locking assembly disconnected from the inner tube driving member in the implant delivery device according to Embodiment 1 of the present invention.

Reference is now made to FIGS. 1 to 4, in which FIG. 1 is a schematic illustration of an implant delivery device according to Embodiment 1 of the present invention; FIG. 2 is a diagram schematically illustrating an air-evacuation locking assembly coupled to an inner tube driving member in the implant delivery device according to Embodiment 1 of the invention; FIG. 3 is an enlarged view of portion M of the implant delivery device of FIG. 2; and FIG. 4 is a partial schematic illustrating the air-evacuation locking assembly disconnected from the inner tube driving member in the implant delivery device according to Embodiment 1 of the invention. In FIG. 1, a casing 110 is not shown in order to facilitate a clearer understanding of the internal structure of the implant delivery device.

The implant delivery device 100 according to this Embodiment includes: the casing 110; and an inner tube 120, an intermediate tube 130, an outer tube 140, an inner tube driving member 150, an outer tube driving member 160 and the air-evacuation locking assembly 170, each partially housed in the casing 110. The inner tube 120, the intermediate tube 130 and the outer tube 140 are sequentially nested from inward to outward. The inner tube 120 and the intermediate tube 130 form a first space therebetween. The intermediate tube 130 and the outer tube 140 form a second space therebetween, and the inner tube 120 and the outer tube form a third space therebetween.

The inner tube driving member 150 has a proximal end that is sealingly fixed to a proximal end of the inner tube 120 and is able to drive the inner tube 120 to move axially along the casing 110. The outer tube driving member 160 is sealingly fixed to a proximal end of the outer tube 140 and is able to drive the outer tube 140 to move axially along the casing 110. The intermediate tube 130 has a proximal end that is sealingly fixed to the inner tube driving member 150. Additionally, the intermediate tube 130 extends through the outer tube driving member 160 and is sealed and connected thereto. The air-evacuation locking assembly 170 is detachably coupled to the inner tube driving member 150.

The inner tube driving member 150 is provided with a first air-evacuation channel A (which is preferred to extend radially), and the air-evacuation locking assembly 170 is provided with a second air-evacuation channel B which has an end located outside the casing 110 so as to receive an external air-evacuation medium. When the air-evacuation locking assembly 170 is coupled to the inner tube driving member 150, the other end of the second air-evacuation channel B will be brought into communication with the second and third spaces via the first air-evacuation channel A and the first space so that the external air-evacuation medium can be introduced into the second and third spaces to expel the air out thereof. Moreover, when the air-evacuation locking assembly 170 is coupled to the inner tube driving member 150, the inner tube driving member 150 will be connected to the casing 110 via the air-evacuation locking assembly 170, enabling indirect connection between the inner tube 120 and the casing 110. On the other hand, when the air-evacuation locking assembly 170 is disconnected from the inner tube driving member 150, the inner tube driving member 150 will be slidably coupled to the casing 110. That is, the inner tube driving member 150 can move axially along the casing 110 within the casing 110. It will be appreciated that, in order to introduce the air-evacuation medium into the second air-evacuation channel B, the air-evacuation locking assembly 170 may be coupled to an external device for supplying the air-evacuation medium.

Figure 5:
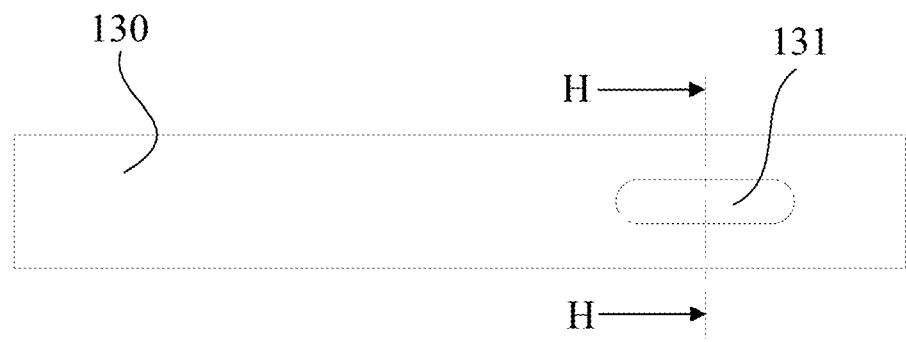
FIG. 5 schematically illustrates an intermediate tube according to Embodiment 1 of the present invention.
Figure 6:
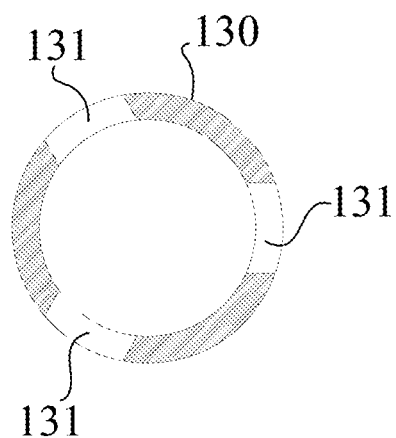
FIG. 6 is a cross-sectional view of the intermediate tube taken along line H-H in FIG. 5.

Preferably, the intermediate tube 130 may define an air-evacuation aperture 131 through which the first space and the second space communicate (apparently, the air-evacuation aperture 131 may extend through the wall of the intermediate tube 130, as more clearly viewed in FIGS. 5 and 6). When the air-evacuation locking assembly 170 is coupled to the inner tube driving member 150, the other end of the second air-evacuation channel B will be brought into communication with the second and third spaces via the first air-evacuation channel A, the first space and the air-evacuation aperture 131.

The implant delivery device 100 of Embodiment 1 will be described in greater detail below with reference to FIGS. 1 to 8.

In this Embodiment, the air-evacuation locking assembly 170 may include a locking member 171 detachably coupled to the inner tube driving member 150. Part of the locking member 171 may be located outside of the casing 110 so as to facilitate a user to manipulate the locking member 171. In particular, the locking member 171 may define a lumen that extends therethrough so as to form the second air-evacuation channel B.

Further, the locking member 171 may include a controller section 1711 and a stopper section 1712. The controller section 1711 may be located outside the casing 110 and connected to the external device at one end and connected to the stopper section 1712 at the other so as to drive the stopper section 1712 to move relative to the inner tube driving member 150. The stopper section 1712 may be accommodated within the casing 110 and engaged with the inner tube driving member 150 under the driving of the controller section 1711.

Furthermore, each of the controller section 1711 and the stopper section 1712 may be hollow (i.e., each of them may define a through lumen). Hereinafter, the lumen of the controller section 1711 will be referred to as the "first lumen", and the lumen of the stopper section 1712 as the "second lumen". In one embodiment of the present invention, the first and second lumens may directly communicate with each other and thus constitute the second air-evacuation channel B. Preferably, the controller section 1711 may be integral with the stopper section 1712.

In this Embodiment, the locking member 171 can not only deliver the air-evacuation medium, but can also lock the inner tube driving member 150 to result in the connection of the inner tube driving member 150 with the casing 110. Of course, when the locking member 171 is disconnected from the inner tube driving member 150, the inner tube driving member 150 is moveable relative to the casing 110. Specifically, the locking member 171 is detachably coupled to the inner tube driving member 150, and when the locking member 171 locks the inner tube driving member 150, the locking member 171 is immobilized with respect to the casing 110 along an axial direction of the latter, making the inner tube driving member 150 unable to move axially along the casing 110. When the locking of the inner tube driving member 150 by the locking member 171 is released, the locking member 171 will be separated from the inner tube driving member 150, allowing the inner tube driving member 150 to move relative to and along the casing 110 axially.

The inner tube driving member 150 may define a receptacle (not labeled) complementary to the stopper section 1712. The receptacle may receive at least part of the stopper 1712 so as to limit axial displacement of the inner tube driving member 150. Moreover, the first air-evacuation channel A may be defined by the receptacle. That is, when the stopper section 1712 is received in the receptacle, the second air-evacuation channel B will be connected to the first air-evacuation channel A. Alternatively, the stopper section 1712 may be implemented as a receptacle, with the inner tube driving member 150 accordingly provided with a protrusion complementary to the stopper section 1712. In this case, a connection of the second air-evacuation channel B and the first air-evacuation channel A can be similarly built by engaging the stopper section 1712 with the inner tube driving member 150.

Preferably, in this Embodiment, an end portion of the stopper section 1712 facing the receptacle may assume the shape of a tapered protrusion engageable with the receptacle of the inner tube driving member 150. This provides a simple structure allowing smooth engagement of the stopper section 1712 with the receptacle.

In one embodiment, a guide member 180 may be provided in and fixed to the casing 110. The guide member 180 may define a through-out guide channel (not labeled) and have a width matching a width of the stopper section 1712. Additionally, the guide channel may be aligned with the first air-evacuation channel A defined by the receptacle of the inner tube driving member 150 so that the stopper section 1712 can move, under the driving of the controller section 1711, along a direction in which the guide channel extends, thereby resulting in the locking of the inner tube driving member 150.

Preferably, the stopper section 1712 may engage with the guide channel by a threaded connection. In other words, when the controller section 1711 is rotated, the stopper section 1712 will be threadedly engaged with the guide channel. As a result, the stopper section 1712 can be controlled to be locked against the inner tube driving member 150 and fixed to the casing 110.

Preferably, the locking member 171 may further include a flow control member 1713 disposed within the second air-evacuation channel B and configured to control a flow direction of the air-evacuation medium. Preferably, the flow control member 1713 may include a one-way check valve or a controllable lock valve.

Figure 7:
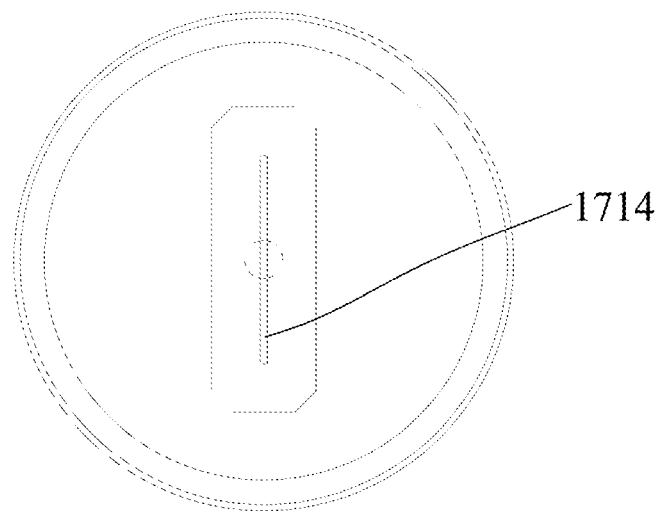
FIG. 7 is a schematic representation of a one-way check valve according to an example of Embodiment 1 of the present invention.
Figure 8:
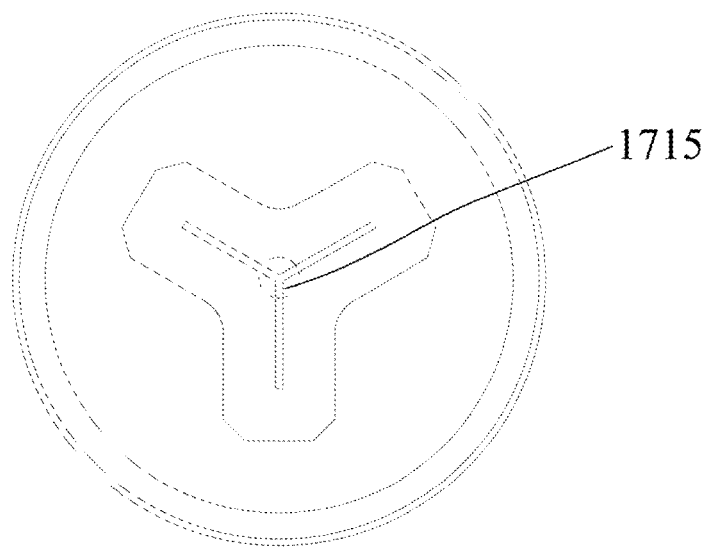
FIG. 8 schematically depicts another one-way check valve according to a preferred example of Embodiment 1 of the present invention.

FIG. 7 is a schematic representation of a one-way check valve according to Embodiment 1 of the present invention, and FIG. 8 schematically depicts another one-way check valve of Embodiment 1 of the present invention. The one-way check valve of FIG. 7 comprises an I-shaped check orifice 1714, while the check valve of FIG. 8 comprises a Y-shaped check orifice 1715. Of course, the present invention is not limited to the one-way check valves of FIGS. 7 and 8, and any other valve capable of unidirectional check can also be suitably used. According to this Embodiment, a controllable lock valve may be alternatively used. The controllable lock valve may have a check orifice which can be opened or closed by the user to control the flow direction of the air-evacuation medium.

In this Embodiment, the external air-evacuation medium may sequentially flow through at least the second air-evacuation channel B, the first air-evacuation channel A and the first space into the second and third spaces. Preferably, part of the air-evacuation medium may sequentially flow through the second air-evacuation channel B, the first air-evacuation channel A, the first space and the air-evacuation aperture 131 into the second space and then into the third space, while the remainder of the air-evacuation medium may sequentially through the second air-evacuation channel B, the first air-evacuation channel A and the first space and then directly enter the third space.

In this Embodiment, the air-evacuation aperture 131 may be preferably oblong, as shown in FIG. 5. More preferably, a plurality of, e.g., three air-evacuation apertures 131 may be formed, as shown in FIG. 6. Preferably, the plurality of air-evacuation apertures 131 may be uniformly distributed along a circumference of the intermediate tube 130. FIG. 5 is a schematic illustration of the intermediate tube according to Embodiment 1 of the present invention, and FIG. 6 is a cross-sectional view of the intermediate tube of FIG. 5 taken along line H-H.

In addition, it should be appreciated that a distal end of the inner tube 120 protrudes out of the intermediate tube 130 and defines the third space together with the outer tube 140 and that the proximal end of the intermediate tube 130 extends out of the outer tube 140 and is connected to the inner tube driving member. Moreover, the intermediate tube 130 shall be long enough to ensure that, when the outer tube driving member 160 is driven to move to a distal end of the casing 110, there is still part of the intermediate tube 130 covered by the outer tube 140. Further, in the case that the intermediate tube 130 defines the air-evacuation aperture 131, the air-evacuation aperture 131 may be preferably also covered by the outer tube 140. In this Embodiment, the air-evacuation aperture 131 may be preferably defined at a distal end of the intermediate tube 130.

With continued reference to FIG. 2, the inner tube driving member 150 may be disposed at a proximal end of the casing 110 and comprise a third lumen and a fourth lumen. The third lumen axially extends through the inner tube driving member 150. The fourth lumen constitutes the first air-evacuation channel A and communicates with the first space. Preferably, a central axis of the third lumen may be perpendicular to central axis of the fourth lumen.

In this Embodiment, the proximal end of the inner tube 120 may be inserted in the third lumen, and fixed and sealed (e.g., welded, bonded, riveted, or otherwise fixed and sealed) to the proximal end of the inner tube driving member 150. A proximal end of the third lumen may coincide with the proximal end of the inner tube 120. Meanwhile, the intermediate tube 130 may be accordingly inserted in the third lumen, with its proximal end coincident with a distal end of the third lumen and adjacent to the fourth lumen. In this way, when leaving the first air-evacuation channel A, the air-evacuation medium will directly enter the first space between the inner tube 120 and the intermediate tube 130.

Optionally, the intermediate tube 130 may be fixed and sealed at the proximal end to the inner tube driving member 150 by welding, riveting, bonding, a sealing ring or the like.

In a preferred embodiment, the intermediate tube 130 may extend distally from the inner tube driving member 150, pass through the outer tube driving member 160 and be sealingly connected to the outer tube driving member 160 so as to prevent the air-evacuation medium from leaking out from the second space. In case of the intermediate tube 130 defining the air-evacuation aperture 131, the intermediate tube 130 may be sealingly connected to the outer tube driving member 160 at a proximal end of the air-evacuation aperture 131. The intermediate tube 130 may be sealingly connected to the outer tube driving member 160, for example, by a sealing ring 190.

Further, an axially-extending portion of the inner tube driving member 150 may protrude out of the casing 110 and can be manipulated by the user to retract or advance the inner tube 120 axially. Furthermore, the inner tube 120 may be coupled at the proximal end to the external device by a luer taper connection so as to allow the air-evacuation medium to be introduced into the inner tube 120 to expel the air out of the system. Optionally, the external device may be provided with an air-evacuation introduction pipe connected to the proximal end of the inner tube 120. In order to prevent backflow, another flow control member (not shown) may be disposed between the air-evacuation introduction pipe and the inner tube 120 so as to guarantee unidirectional flow of the air-evacuation medium. The flow control member may be implemented as, e.g., a one-way check valve or a controllable lock valve.

With continued reference to FIGS. 2 and 3, the outer tube driving member 160 may be disposed distally from the inner tube driving member 150 within the casing 110 and comprise a fifth lumen extending therethrough axially. The outer tube driving member 160 may drive the outer tube to move axially along the casing 110 so as to enable the loading and deployment of a prosthetic heart valve. The outer tube 140 may be inserted at the proximal end in the fifth lumen and sealingly fixed to the outer tube driving member 160. Optionally, the outer tube 140 may be sealingly fixed to the outer tube driving member 160 by welding, riveting, bonding, a sealing ring or the like. Accordingly, the intermediate tube 130 may extend from the inner tube driving member 150 through the fifth lumen so as to ensure that the distal end of the intermediate tube 130 is always covered by the outer tube 140. Further, in case of the intermediate tube 130 defining the air-evacuation aperture 131, preferably, the air-evacuation aperture 131 may also be always covered by the outer tube 140.

In a preferred embodiment, in case of the proximal end of the intermediate tube 130 sealingly fixed to the inner tube driving member 150, the distal end of the intermediate tube 130 may be fixed but not sealed to the inner tube 120. For example, the distal end of the intermediate tube 130 may be fixed but not sealed to the inner tube 120 with respect to the right side of the air-evacuation aperture 131 (i.e., on the side thereof far away from the proximal end of the intermediate tube 130). As part of the first space between the inner tube 120 and the intermediate tube 130 is located at the right side of the air-evacuation aperture 131, in addition to via the air-evacuation aperture 131 and the second space, the air-evacuation medium can also directly enter the third space between the inner tube 120 and the outer tube 140 via said part of the first space. This arrangement can not only maintain the concentricity of the intermediate tube 130 and the inner tube 120 but can also prevent the intermediate tube 130 from acting like a cantilever beam and thus causing uneven stress. It can further allow the air-evacuation medium to flow from the first space between the distal end of the intermediate tube 130 and the inner tube 120 into the third space between the inner tube 120 and the outer tube 140, expanding the volume in which it can flow. Optionally, the intermediate tube 130 is fixed to the inner tube 120 by riveting, welding, bonding or the like.

The present invention is not limited to any particular structure or configuration of the distal-end portions of the inner and outer tubes protruding out of the casing, and those of ordinary skill in the art may select a suitable structure according to the type of the implant, the target site and etc.

In this Embodiment, the distal-end portion of the inner tube 120 may include an anchor 121, a distal section of the inner tube 122 coupled to the anchor 121 and a conical tip 123 disposed at a distal end of the distal section of the inner tube 122. The anchor 121 may define a recess in which the implant can be loaded. At the distal end of the outer tube 140 may be disposed a sheath 141 for constraining the implant in a crimped configuration. The sheath 141 may have a length matching a length of the distal section of the inner tube 122.

An operational process of the implant delivery device 100 according to this Embodiment will be described below in conjunction with the structural details thereof as set forth above.

Air Evacuation: the distal-end portions of the outer and inner tubes 140, 120 are immersed into the air-evacuation medium (which is for example water, and the distal-end portions are thus brought into, for example, an aqueous environment). The air-evacuation medium is then driven into the first, second and third spaces by the air-evacuation locking assembly 170 so as to expel the air between the outer and inner tubes 140, 120 out of the system. The air-evacuation medium is also introduced into a lumen of the inner tube 120 via the Luer taper so as to expel the air there.

Loading of Implant: locking lugs of the implant are first hooked on the anchor 121 of the inner tube 120, and the outer tube 140 is then caused to move toward a distal end of the implant delivery device 100 so that the sheath 141 sleeves the distal section of the inner tube 122 and the implant over the distal section of the inner tube 122. As a result, the implant is crimped and restrained between the outer tube 140 and the inner tube 120.

Delivery and Deployment of Implant: subsequent to the loading of the implant, the implant is delivered into the patient's body with the inner tube 120 kept stationary with respect to the outer tube 140. After the implant is advanced to the target site, the outer tube 140 is manipulated to move toward a proximal end of the implant delivery device 100, causing the sheath 141 to slide away from the implant. Released from the constrained stress of the sheath 141, the implant will self-expand and steadily remain at the lesion site.

Retrieval of the delivery device: after the implant is deployed at the lesion site, the inner tube driving member 150 is unlocked from the air-evacuation locking assembly 170 and is operated to cause the inner tube 120 to move toward the proximal end of the implant delivery device 100. As a result, a proximal end of the conical tip 123 abuts the distal end of the outer tube 140, achieving closure of the distal ends of the inner tube 120 and the outer tube 140, followed by retrieval of the delivery device from the patient's body.

In the embodiments disclosed hereinabove, the casing 110 may be implemented as, for example, a handle and serve as a base to which the various components of the implant delivery device 100 are mounted or attached. For example, the inner tube driving member 150 and the outer tube driving member 160 may be disposed within the casing 110 in such a manner that they are able to move axially along and relative to the casing 110. The inner tube 120 may be coupled at the proximal end to the inner tube driving member 150, with its distal end protruding out of the distal end of the casing 110. The outer tube 140 may be coupled at the proximal end to the outer tube driving member 160, with its distal end also protruding out of distal end of the casing 110. The air-evacuation locking assembly 170 may be partially housed in the casing 110 and movable relative to the casing 110. The present invention is not limited to any particular material, shape or size of the casing 110, and any existing or future-developed structure that is suitable to be held and manipulated by the user and capable of accommodating part of the inner tube 120, the intermediate tube 130, part of the outer tube 140 and other components can be suitably used as the casing 110 in the inventive implant delivery device 100.

In this Embodiment, the implant delivery device 100 may further include a movement control member and a move guide track disposed on the casing 110. The movement control member may be movably disposed on the move guide track and coupled to the outer tube driving member 160. The user may manipulate the movement control member so that the movement control member moves along the move guide track to cause the outer tube driving member 160 and hence the outer tube 140 to move in synchronization.

In the embodiments disclosed hereinabove, the intermediate tube 130 may be made of a polymeric or metallic material. The metallic material may either be a metal, such as stainless steel, titanium or gold, or an alloy such as nickel-titanium or cobalt-nickel. The polymer material may be one or more of polycarbonate, polypropylene, polyamide, polyimide, an acrylonitrile-butadiene-styrene copolymer. Of course, those skilled in the art will appreciated that the intermediate tube 130 may also be made of any suitable material that may be developed in the future and selected based on the environmental requirements of the implantation process.

Further, each of the outer tube 140 and inner tube 120 may be composed of multiple braided layers or fabricated from a metal, a macromolecular compound or another chemical material suitable for medical use. In general terms, the outer tube 140 and the inner tube 120 are both required to have high axial stretch resistance and a certain degree of bendability in the direction perpendicular to the axial direction.

Embodiment 2

Figure 9:
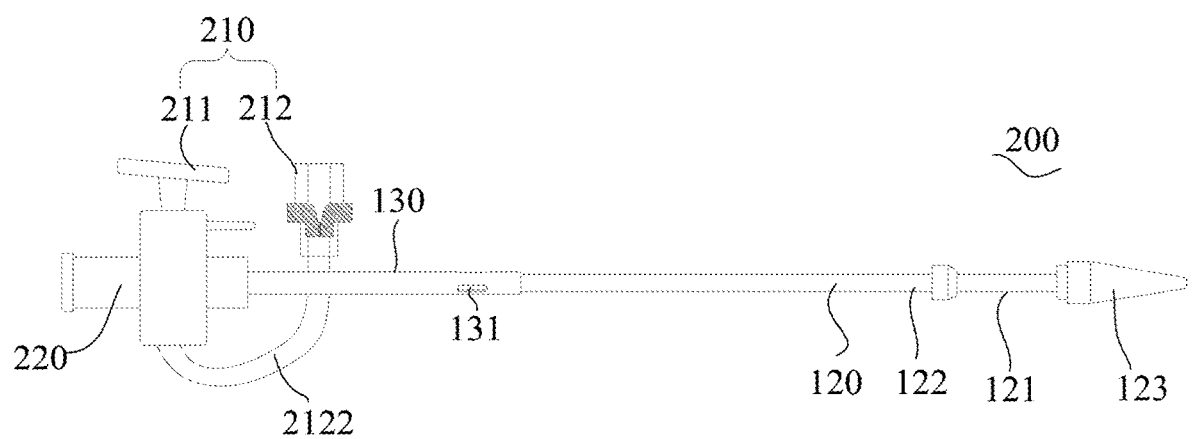
FIG. 9 is a schematic illustration of an implant delivery device according to Embodiment 2 of the present invention, in which a casing is not shown.
Figure 10:
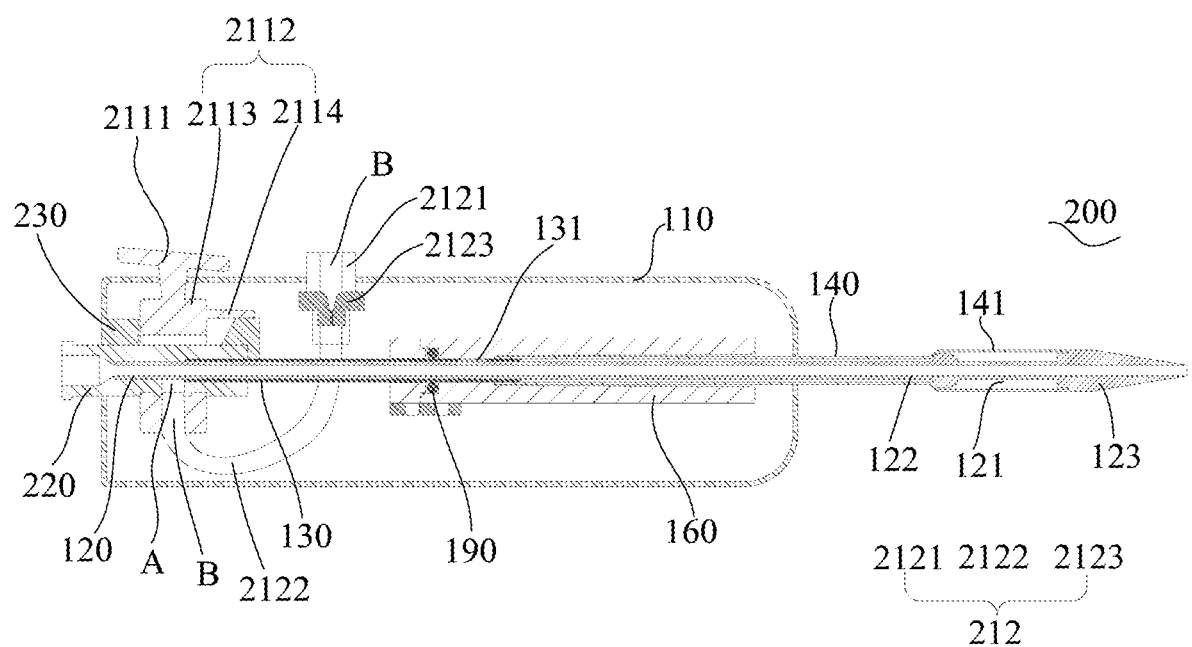
FIG. 10 is a diagram schematically illustrating an air-evacuation locking assembly connected to an inner tube driving member in the implant delivery device according to Embodiment 2 of the present invention.
Figure 11:
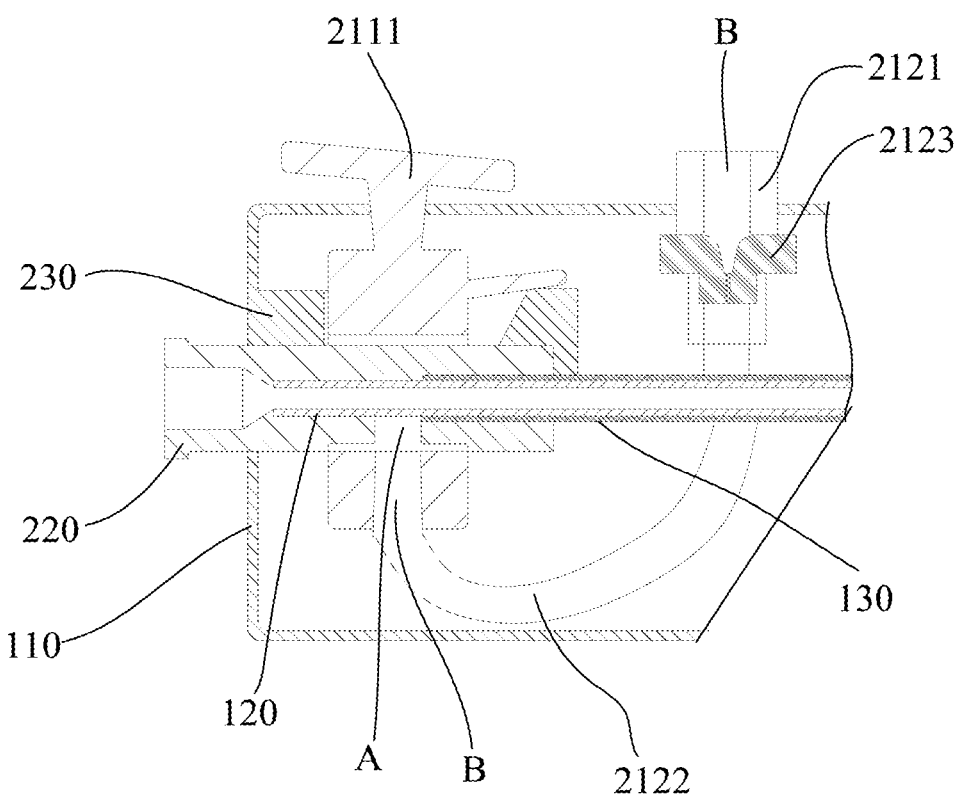
FIG. 11 is a partial schematic illustrating the air-evacuation locking assembly disconnected from the inner tube driving member in the implant delivery device according to Embodiment 2 of the present invention.

FIG. 9 is a schematic illustration of an implant delivery device according to Embodiment 2 of the present invention. FIG. 10 is a diagram schematically illustrating an air-evacuation locking assembly connected to an inner tube driving member in the implant delivery device according to Embodiment 2 of the present invention. FIG. 11 is a partial schematic illustrating the air-evacuation locking assembly disconnected from the inner tube driving member in the implant delivery device according to Embodiment 2 of the present invention. FIG. 9 omits a casing 110, an outer tube 140 and an outer tube driving member 160. This Embodiment differs from Embodiment 1 essentially in the structure of the air-evacuation locking assembly, and reference can be made to Embodiment 1 for similar structural details therebetween.

In the implant delivery device 200 of this Embodiment, the air-evacuation locking assembly 210 includes a locking member 211 and a fluidic member 212. The locking member 211 is detachably coupled to the inner tube driving member 220 and interconnected with the fluidic member 212.

Different from Embodiment 1, the air-evacuation locking assembly 210 includes the locking member 211 and the fluidic member 212. The fluidic member 212 may have a portion that is situated out of the casing 110 and configured to introduce an air-evacuation medium. Similarly, the locking member 211 may also have a portion protruding out of the casing 110, which is configured to facilitate the user's manipulation of the locking member 211. Different from Embodiment 1, the locking member 211 may have a sixth lumen, which is brought into communication with a first air-evacuation channel A when the locking member 211 is coupled to the inner tube driving member 220. The fluidic member 212 may comprise a seventh lumen extending through the fluidic member. The sixth and seventh lumens may communicate with each other to form a second air-evacuation channel B.

In addition, similar to Embodiment 1, the locking member 211 may include a controller section 2111 and a stopper section 2112. The stopper section 2112 may be configured to be engaged with the inner tube driving member 220, and the controller section 2111 may be configured to drive the stopper section 2112 to move. Similarly, one end of the controller section 2111 may protrude out of the casing 110 to facilitate the user's manipulation. However, differing from Embodiment 1, the sixth lumen is provided only by the stopper section 2112. When the stopper section 2112 is engaged with the inner tube driving member 220, the sixth lumen is brought into communication with the first air-evacuation channel A.

Further, the stopper section 2112 may further comprise an eighth lumen axially extending therethrough, which allows the locking member 211 to directly sleeve over the inner tube driving member 220. The eighth lumen may communicate with the sixth lumen and preferably have a central axis that is perpendicular to a central axis of the sixth lumen.

In a preferred embodiment, the stopper section 2112 may include a stopper body 2113 and an elastic structure 2114. The stopper body 2113 is configured to be engaged with the inner tube driving member 220. The stopper body 2113 comprises the sixth lumen. The elastic structure 2114 is coupled to the stopper body 2113. The stopper section 2112 may be kept in connection with the inner tube driving member 220 through the elastic structure 2114. When the elastic structure 2114 is stressed, the stopper section 2112 is to be disengaged from the inner tube driving member 220 through the elastic structure 2114.

Further, similar to Embodiment 1, the inner tube driving member 220 may define a third lumen, a fourth lumen and a receptacle. The third lumen axially extends through the inner tube driving member 220. The fourth lumen is in communication with the third lumen. Axially, the stopper body 2113 may have a width matching a width of the receptacle. The fourth lumen may serve as the first air-evacuation channel A and be defined by the receptacle (e.g., the receptacle may comprise a T-shaped structure with a vertical portion constituting the first air-evacuation channel A and a horizontal portion for engagement with the stopper body 2113). When the stopper body 2113 is engaged with the inner tube driving member 220, the first air-evacuation channel A will be brought into communication with the second air-evacuation channel B, allowing the external air-evacuation medium to flow through the second air-evacuation channel B, the first air-evacuation channel A and a first space (between an inner tube 120 and an intermediate tube 130) into a second space (between the intermediate tube 130 and an outer tube 140) and then into a third space (between the inner tube 120 and the outer tube 140). As shown in FIG. 10, different from the embodiment shown in FIG. 2, an air-evacuation aperture 131 in the intermediate tube 130 may not be covered by the outer tube 140. In this case, part of the air-evacuation medium will flow sequentially through the second air-evacuation channel B, the first air-evacuation channel A, the first space and the air-evacuation aperture 131 into a gap between the intermediate tube 130 and the outer tube driving member 160. Since the intermediate tube 130 and the outer tube 140 are both sealingly connected to the outer tube driving member 160, a confined space is formed, and the air-evacuation medium that has entered the gap between the intermediate tube 130 and the outer tube driving member 160 will continue to flow into the second space between the intermediate tube 130 and the outer tube 140 and then into the third space. On the other hand, the remainder of the air-evacuation medium will flow directly into the third space sequentially through the second air-evacuation channel B, the first air-evacuation channel A and the first space.

In this Embodiment, the elastic structure 2114 may include an elastic finger made of an elastic material. One end of the elastic finger may be connected to the stopper body 2113, and the other end thereof may be brought into contact with a support member 230 which is disposed within and fixed to the casing 110. Alternatively, the elastic structure 2114 may be implemented as a spring connected to the stopper body 2113 at one end and brought into contact with the support member 230 at the other end. The spring can provide a biasing force enabling the engagement of the stopper body 2113 with the inner tube driving member 220. To sum up, the stopper body 2113 is engaged with the inner tube driving member 220 by the elastic structure 2114. When the biasing force provided by the elastic structure 2114 is overcome by the controller section 2111, the stopper section 2112 will be driven to move downward, causing the stopper body 2113 to be disengaged from the receptacle in the inner tube driving member 220. As a result, the inner tube driving member 220 will be axially moveable along the casing 110.

In this Embodiment, the fluidic member 212 may include a body of fluidic member 2121 and a connecting pipe 2122. The body of fluidic member 2121 defines a lumen extending axially therethrough. The connecting pipe 2122 is connected to the body of fluidic member 2121 at one end and to the stopper section 2112 at the other end. The lumen of the body of fluidic member 2121 may communicate with the interior of the connecting pipe 2122 and constitute, together with the interior of the connecting pipe, the seventh lumen. Further, the seventh and sixth lumens may together constitute the second air-evacuation channel B. In this Embodiment, the body of fluidic member 2121 may be secured to the casing 110, and a portion thereof may protrude outside the casing 110 and connect the external device so as to receive the air-evacuation medium.

The fluidic member 212 may further include a flow control member 2123 disposed on the body of fluidic member 2121 so as to limit and control the flow direction of the air-evacuation medium. Preferably, the flow control member 2123 may include a one-way check valve or a controllable lock valve. More preferably, the flow control member 2123 may be integral with the body of fluidic member 2121.

While a few preferred embodiments of the present invention have been described above, the present invention is not limited to the scope of these disclosed embodiments. Those skilled in the art will appreciate that any other approach allowing engagement or disengagement between the locking member and the inner tube driving member may also be incorporated herein by reference.

Additionally, those skilled in the art will appreciate that the inner and outer tubes according to the present invention match each other in terms of diameter and length, and a determination in this regard shall be properly made based on the environment of the actual implantation procedure.

In the embodiments disclosed hereinabove, it is to be noted that if two elements are described as being "sealingly connected to" each other, it is meant that they are sealed against, while being movable relative to, each other. If two elements are described as being "sealingly fixed to", it is meant that they are so sealed against each other that they cannot move relative to each other.

Compared with the prior art, the inner tube in the implant delivery device of the present invention can be either coupled to or made movable relative to the casing by virtue of the engagement or disengagement between the inner tube driving member and the air-evacuation locking assembly, depending on the actual need. As such, when the delivery device is retrieved after the deployment of implant, the outer tube is kept stationary, the inner tube driving member can be unlocked from the air-evacuation locking assembly such that the inner tube can be moved in the casing and further to drive the inner tube to approach, abut against and thereby close the outer tube, then the delivery device is retrieved from the patient's body. Specifically, since the sheath arranged at the distal end of the outer tube is required to constrain the implant in a crimped configuration, it is necessary for the sheath to be relatively rigid. For this reason, conventionally, driving the inner and outer tubes to abut each other to achieve the closure after the deployment of the implant tends to cause secondary damage to the patient's body by the sheath. In contrast, according to the present invention, the inner tube has smaller size and is made of a more bendable and softer material and the inner tube is allowed by a displacement to abut at the distal end against the distal end of the outer tube and hence close the outer tube. This can lower the risk of secondary damage to the patient's body during retrieval. In addition, in the implant delivery device of the present invention, the second air-evacuation channel arranged in the air-evacuation locking assembly is brought into communication with the second space between the intermediate tube and the outer tube and the third space between the outer tube and the inner tube via the first air-evacuation channel in the inner tube driving member and the first space between the intermediate tube and the inner tube, enabling evacuation of the air from between the inner tube and the outer tube. By using the air-evacuation locking assembly in replace of an air-evacuation hose, this design solves the problem of a deformed or clogged air-evacuation path that may make it hardly possible to expel the air out of the system, arising from the use of the air-evacuation hose. Further, this integral design of the air-evacuation and locking integrates the air-evacuation and locking functions, thus reducing the number of required components and simplifying the operational process. As a result, the delivery device can be more conveniently used with increased performance robustness.

The description presented above is merely that of some preferred embodiments of the present invention and does not limit the scope thereof in any sense. Any and all changes and modifications made by those of ordinary skill in the art based on the above teachings fall within the scope as defined in the appended claims.

What is claimed is:

1. An implant delivery device, comprising:
   a casing; and
   an inner tube driving member, an outer tube driving member, an inner tube, an intermediate tube, an outer tube and an air-evacuation locking assembly, each at least partially accommodated in the casing;
   the inner tube, the intermediate tube and the outer tube are sequentially nested from inside to outside, the inner tube and the intermediate tube form a first space therebetween, the intermediate tube and the outer tube form a second space therebetween, and the inner tube and the outer tube form a third space therebetween, wherein:
   the inner tube driving member has a proximal end that is sealingly fixed to a proximal end of the inner tube, the outer tube driving member sealingly fixed to a proximal end of the outer tube, the intermediate tube having a proximal end that is sealingly fixed to the inner tube driving member, the intermediate tube extending through, and sealingly connected to, the outer tube driving member, the air-evacuation locking assembly detachably coupled to the inner tube driving member, the inner tube driving member is provided with a first air-evacuation channel, the air-evacuation locking assembly provided with a second air-evacuation channel, the second air-evacuation channel protruding out of the casing at a first end and brought, at a second end, into communication with the second and third spaces via the first air-evacuation channel and the first space when the air-evacuation locking assembly is coupled to the inner tube driving member, the inner tube driving member axially fixable relative to the casing through the air-evacuation locking assembly and, when the air-evacuation locking assembly is disconnected from the inner tube driving member, the inner tube driving member is axially slidable along the casing.

2. The implant delivery device of claim 1, wherein the air-evacuation locking assembly comprises a locking member detachably coupled to the inner tube driving member, the locking member comprising a lumen which extends through the locking member to form the second air-evacuation channel.

3. The implant delivery device of claim 2, wherein the locking member comprises a stopper section detachably connectable to the inner tube driving member and a controller section for driving the stopper section to move, the controller section having a first end located outside the casing and provided with a first lumen extending through the controller section, the stopper section provided with a second lumen extending through the stopper section, the first lumen and the second lumen communicating with each other to form the second air-evacuation channel.

4. The implant delivery device of claim 3, further comprising a guide member provided within the casing, the guide member comprising a guide channel extending therethrough, the stopper section being movable relative to the inner tube driving member along an extending direction of the guide channel.

5. The implant delivery device of claim 1, wherein the inner tube driving member comprises a third lumen and a fourth lumen, the third lumen axially extending through the inner tube driving member, the third lumen having a distal end in coincidence with the proximal end of the intermediate tube and a proximal end in coincidence with the proximal end of the inner tube, the fourth lumen constituting the first air-evacuation channel and communicating with the first space.

6. The implant delivery device of claim 1, wherein the outer tube driving member comprises a fifth lumen extending therethrough axially, in which the proximal end of the outer tube is located, and wherein the intermediate tube extends from the inner tube driving member through the fifth lumen.

7. The implant delivery device of claim 1, wherein the air-evacuation locking assembly comprises a locking member detachably coupled to the inner tube driving member and a fluidic member in fixed connection with the locking member, the locking member having a portion situated out of the casing and comprising a sixth lumen in communication with the first air-evacuation channel, the fluidic member comprising a seventh lumen extending therethrough, the sixth and seventh lumens communicating with each other to form the second air-evacuation channel.

8. The implant delivery device of claim 7, wherein the locking member comprises a stopper section detachably connectable to the inner tube driving member and a controller section for driving the stopper section to move, the controller section having a first end located outside the casing, the stopper section provided with the sixth lumen.

9. The implant delivery device of claim 8, wherein the stopper section comprises a stopper body detachably coupled to the inner tube driving member and an elastic structure coupled to the stopper body, the stopper section connected to the inner tube driving member via the elastic structure and, when the elastic structure is stressed, the stopper section is disconnected from the inner tube driving member.

10. The implant delivery device of claim 1, wherein the air-evacuation locking assembly comprises a flow control member for controlling a flow direction of an air-evacuation medium, the flow control member disposed in the second air-evacuation channel.

11. The implant delivery device of claim 10, wherein the flow control member comprises a one-way check valve or a controllable lock valve.

12. The implant delivery device of claim 1, wherein the intermediate tube is provided with, at the distal end, an air-evacuation aperture through which the first space communicates with the second space, and wherein when the air-evacuation locking assembly is coupled to the inner tube driving member, the second end of the second air-evacuation channel is brought into communication with the second and third spaces via the first air-evacuation channel, the first space and the air-evacuation aperture.

13. The implant delivery device of claim 12, wherein the intermediate tube comprises a plurality of air-evacuation apertures that are uniformly distributed around a circumference of the intermediate tube.

14. The implant delivery device of claim 1, wherein the distal end of the intermediate tube is fixed but not sealed to the inner tube.

15. The implant delivery device of claim 1, further comprising a movement control member and a move guide track, the move guide track disposed on the casing, the movement control member movably disposed on the move guide track and coupled to the outer tube driving member.

* * * * *